(12) United States Patent
Lu

(10) Patent No.: US 12,257,255 B1
(45) Date of Patent: Mar. 25, 2025

(54) TIMOLOL MALEATE GEL FOR TOPICAL ADMINISTRATION

(71) Applicant: Auson Pharmaceuticals, Inc., Bridgewater, NJ (US)

(72) Inventor: Enxian Lu, East Brunswick, NJ (US)

(73) Assignee: AUSON PHARMACEUTICALS INC., Bridgewater, NJ (US)

( * ) Notice: Subject to any disclaimer, the term of this patent is extended or adjusted under 35 U.S.C. 154(b) by 0 days.

(21) Appl. No.: 18/420,370

(22) Filed: Jan. 23, 2024

(51) Int. Cl.
  *A61K 31/5377* (2006.01)
  *A61K 9/00* (2006.01)
  *A61P 9/14* (2006.01)

(52) U.S. Cl.
  CPC ........ *A61K 31/5377* (2013.01); *A61K 9/0014* (2013.01); *A61P 9/14* (2018.01)

(58) Field of Classification Search
  CPC ...... A61K 31/5377; A61K 9/0014; A61P 9/14
  See application file for complete search history.

(56) References Cited

U.S. PATENT DOCUMENTS

| 8,338,489 | B2 | 12/2012 | Leaute-Labreze et al. |
| 8,987,262 | B2 | 3/2015 | Leaute-Labreze et al. |

FOREIGN PATENT DOCUMENTS

| CN | 105106105 A | 12/2015 |
| CN | 105998178 A | 10/2016 |
| CN | 107281094 A | 10/2017 |

OTHER PUBLICATIONS

Thomas et al., Journal of Vascular Surgery, 2017, 844-850.*

\* cited by examiner

*Primary Examiner* — Shobha Kantamneni
(74) *Attorney, Agent, or Firm* — FOX ROTHSCHILD LLP

(57) ABSTRACT

A formulation for topical administration of timolol maleate is disclosed. The formulation, when administered at a daily dose from about 0.4 to about 15 mg/cm²/day, provides a steady state mean timolol blood $C_{max,ss}$ below 3 ng/ml in a subject in need thereof, wherein at steady state the ratio of $C_{max,SS}/C_{min,SS}$ is less than 2. Also disclosed herein is a method of treating skin conditions such as infantile hemangiomas and chronic venous leg ulcer.

10 Claims, 2 Drawing Sheets

TIMOLOL MALEATE GEL FOR TOPICAL ADMINISTRATION

FIELD OF THE INVENTION

This patent document provides a formulation of timolol maleate for topical administration to treat infantile hemangiomas and chronic venous leg ulcer. The formulation and its administration are designed to provide a suitable pharmacokinetic profile for effective treatment with minimum side effects.

BACKGROUND ART

Infantile hemangiomas (IH) are common benign vascular endothelial cell proliferative tumors. The lesions are mostly present in the head and neck of infants, relatively superficial, with an incidence of 2.5%~12% in neonates. The specific location of the lesions often leads to the involvement of vital organs, and in severe cases, it may endanger the patient's life, bringing enormous physiological pain and mental pressure to the patients and their family members.

There are some options available for treating infantile hemangiomas, and systemic drug therapy has traditionally been the first choice. Corticosteroids, interferon, and vincristine have been used in the treatment of infantile hemangiomas, but the complications they may cause have limited their widespread clinical use.

Timolol maleate (TM) was firstly used locally for the treatment of infantile hemangiomas by L'aut'-Labr'ze, et al. in 2008, and gained significant therapeutic effect. Thereafter, a large number of clinical trials were performed on the treatment of infantile hemangiomas with timolol maleate and achieved consistent therapeutic results. The topical preparation of timolol maleate has gradually become the most effective substitute for oral propranolol in the treatment of infantile hemangiomas.

However, timolol maleate is currently available only in three dosage forms: tablets, eye drops and eye gel drops. Oral timolol has potential cardiotoxic side effects and may induce adverse reactions, moreover, infantile patients with hemangiomas have poor medication compliance. Eye drops and eye gel drops are less effective due to their fluid nature and inconvenient dermal application, and they are likely to cause a decrease in intraocular pressure when applied around the eyes.

A need exists for an effective formation for topic administration in the treatment of diseases such as infantile hemangiomas and chronic venous leg ulcer. Preferably, the formulation will also overcome side effects as observed in conventional formulation which compromise patient compliance.

SUMMARY OF THE INVENTION

The formulation disclosed in this patent document addresses the needs. By providing a suitable pharmacokinetic profile, the formulation effectively treats skin conditions with minimum side effects.

An aspect of the patent document provides a method of providing a steady state mean timolol blood $C_{max,ss}$ below 3 ng/ml in a subject in need thereof. The method includes administering topically to the subject a formulation comprising timolol maleate at a daily dose ranging from about 0.4 to about 15 mg/cm$^2$/day, wherein the formulation is configured and the amount of the timolol maleate in the formulation is selected so that at steady state a ratio of $C_{max,SS}/C_{min,SS}$ is less than 2.

In some embodiments, the formulation is configured and the amount of the timolol maleate in the formulation is selected so that the mean $C_{max,ss}$ is less than 1500 pg/mL, less than 300 pg/mL, or less than 150 pg/mL. In some embodiments, the daily dose ranges from about 0.5 to about 8 mg/cm$^2$/day, wherein the mean $C_{max,ss}$ is less than 150 μg/mL.

In some embodiments, the formulation contains a daily dose of timolol ranging from about 0.4 to about 10 mg/cm$^2$/day or from about 0.5 to about 8 mg/cm$^2$/day.

In some embodiments, the formulation is administered 1-5 times a day, 2-3 times a day, or 2 times a day.

In some embodiments, the subject is of an age of 3-12 month. In some embodiments, the subject has been diagnosed of infantile hemangiomas. In some embodiments, the subject has been diagnosed with chronic venous leg ulcer.

In some embodiments, the formulation is in the form of a gel. In some embodiments, the formulation is free from a permeation enhancer.

In some embodiments, the formulation comprises propylene glycol in an amount ranging from 5% to 7% by weight, carbomer in an amount ranging from 1.6% to 2.5% by weight, triethanolamine in an amount ranging from 0.6% to 1.0% by weight, and ethyl hydroxybenzoate in an amount ranging from 0.05% to 2% by weight. In some embodiments, the formulation comprises propylene glycol in an amount of about 6% by weight carbomer in an amount of about 1.8% by weight, triethanolamine in an amount of about 0.8% by weight, and ethyl hydroxybenzoate in an amount of about 0.1% by weight.

In some embodiments, the daily dose ranges from about 0.5 to about 8 mg/cm$^2$/day, wherein the mean $C_{max,ss}$ is less than 150 pg/mL.

In some embodiments, the formulation is prepared according to the following steps:
a. Add the prescription amount of timolol maleate in water, stir and dissolve to obtain a clear and transparent solution I;
b. Add the prescription amount of carbomer to solution I and stir to make it fully swollen to obtain a well-dispersed solution II;
c. Add the prescription amount of ethyl hydroxybenzoate to a formulated dosage of propylene glycol, stir and dissolve to obtain a clear and transparent solution III;
d. Add solution III to solution II, stir and mix well to obtain mixture V; and
e. Add the prescription amount of triethanolamine to the mixture V described in step 4), add the remaining amount of water and mix well to obtain the pharmaceutical composition of timolol maleate.

DETAILED DESCRIPTION OF THE DRAWINGS

DETAILED DESCRIPTION OF THE INVENTION

Figure 1:
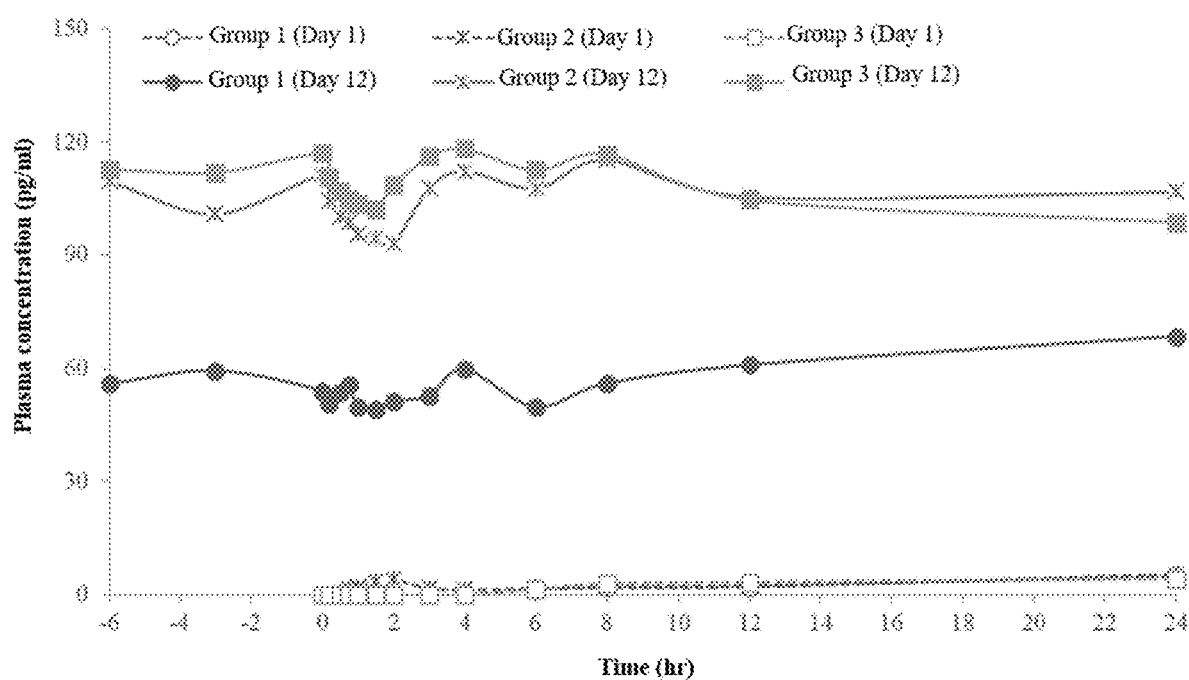
FIG. 1 shows average plasma concentration-time curves of an example timolol gel formulation in healthy subjects by single and multiple topical administrations.

Various embodiments herein disclose formulations of timolol or a pharmaceutically acceptable salt thereof for topical administration. The formulation provides a therapeutically effective amount of timolol topically and reduce PTF without serious adverse events. The formulation is suitable for treating diseases including hemangiomas and chronic venous leg ulcer.

Although the following contents may refer to or exemplify a specific embodiment of a pharmaceutical formulation or dosage form, they are not limited to the specified ranges of the pharmaceutical formulation or dosage form. In view of practicality and economy considerations, a person skilled in the art can make various modifications to, e.g., the content of active ingredients and the dosage regimen of the dosage form for treating diseases or disorders.

Unless otherwise defined, all technical and scientific terms used herein have the same meaning as commonly understood by a person skilled in the field of the present invention. Definitions of various terms include the following.

The term "steady state" means that the blood plasma concentration curve for a given drug does not substantially fluctuate after repeated doses to dose of the formulation.

The term "a", "an" or "the" as used herein means "one or more" or "at least one". That is, reference to any element or composition of the present invention by "a", "an" or "the" does not exclude the possibility of the presence of a plurality of the elements and formulations.

The term "about" and the like as used herein, when used in connection with a numerical variable, generally means that the value of the variable and all values of the variable are within the range of experimental error (e.g., within the 95% confidence interval for the mean) or within ±10% or within ±5% of the indicated value, whichever is greater.

The term "steady state" means that the blood plasma concentration curve for a given drug does not substantially fluctuate after repeated doses to dose of the formulation.

The term "subject" or "patient" refers to a mammal, and can be an animal or a human.

An aspect of the patent document provides a formulation for topical administration of a therapeutically effective amount of timolol or a pharmaceutically acceptable salt thereof. Preferably, the formulation is configured for administration at a daily dosage of about 0.4 to about 15 mg/cm$^2$/day, and the amount of the timolol maleate in the formulation is selected so that at steady state a ratio of $C_{max,SS}/C_{min,SS}$ is less than 2.

In some embodiments, the amount of timolol or a pharmaceutically acceptable salt thereof in the ranges in the formulation from 0.1% to 5%, from 0.2% to 4%, from 0.5% to 3%, from 0.5% to 2.5%, from 0.5% to 2.0%, from 0.5% to 1.5%, or from 1.0% to 2.0% by weight. Nonlimiting examples of the amount of timolol or a pharmaceutically acceptable salt thereof in the formulation by weight include about 0.2%, about 0.4%, about 0.5%, about 0.6%, about 0.7%, about 0.8%, about 1.0%, about 1.2%, about 1.4%, about 1.6%, about 1.8%, about 2.0%, about 2.2%, about 2.4%, about 2.6%, about 2.8%, about 3.0%, and any range between any two of the aforementioned percentage values. In some embodiments, the formulation contains timolol maleate.

The formulation may contain one or more excipients including for example, a solvent, a viscosity or rheology control agent, a stabilizing agent, an anti-bacterial agent, an anti-oxidant agent, a gelling agent, a spreadability enhancer, emulsifier, pH modifier, and water.

In some embodiments, the formulation contains excipients including propylene glycol, carbomer, triethanolamine, and ethyl hydroxybenzoate. As a solvent, the amount of propylene glycol also impacts the rate of the release of the active ingredient and the extent of skin irritation. In some embodiments, propylene glycol ranges from 4% to 10%, from 4% to 8%, or from 5% to 7% by weight in the formulation. Nonlimiting examples of the amount of propylene glycol in the formulation by weight include about 3%, about 4%, about 5%, about 6%, about 7%, about 8%, and any range between any two of the aforementioned percentage values.

In some embodiments, carbomer ranges in the formulation from 1.0% to 4.5%, from 1.5% to 3.5%, from 1.6% to 2.5%, or from 2.0% to 2.5% by weight. Nonlimiting examples of the amount of carbomer in the formulation by weight include about 1.0%, about 1.2%, about 1.4%, about 1.6%, about 1.8%, about 2.0%, about 2.2%, about 2.4%, about 2.6%, about 2.8%, about 3.0%, and any range between any two of the aforementioned percentage values.

In some embodiments, triethanolamine ranges in the formulation from 0.2% to 2.0%, from 0.4% to 1.8%, from 0.6% to 1.5%, or from 0.8% to 1.0% by weight. Nonlimiting examples of the amount of triethanolamine in the formulation by weight include about 0.2%, about 0.4%, about 0.6%, about 0.8%, about 1.0%, about 1.2%, about 1.4%, about 1.6%, about 1.8%, about 2.0%, and any range between any two of the aforementioned percentage values.

In some embodiments, ethyl hydroxybenzoate ranges in the formulation from 0.05% to 2.0%, from 0.05% to 1.5%, from 0.08% to 1.0%, or from 0.1% to 0.5% by weight. Nonlimiting examples of the amount of ethyl hydroxybenzoate in the formulation by weight include about 0.03%, about 0.05%, about 0.08%, about 0.1%, about 0.2%, about 0.3%, about 0.4%, about 0.5%, about 1.0%, about 2.0%, and any range between any two of the aforementioned percentage values.

In some embodiments, the formulation includes propylene glycol in an amount of about 6% by weight carbomer in an amount of about 1.8% by weight, triethanolamine in an amount of about 0.8% by weight, and ethyl hydroxybenzoate in an amount of about 0.1% by weight.

Another aspect of the patent document provides a method of providing a steady state mean timolol blood $C_{max,ss}$ below 3 ng/ml in a subject in need thereof. The method includes administering topically to the subject a formulation comprising timolol maleate at a daily dosage ranging from about 0.4 to about 15 mg/cm$^2$/day, wherein the formulation is configured and the amount of the timolol maleate in the formulation is selected so that at steady state a ratio of $C_{max,SS}/C_{min,SS}$ is less than 3, less than 2.5, less than 2, less than 1.8, or less than 1.5. In some embodiments, the daily dosage ranges from about 0.2 to about 15, from about 0.4 to about 10, from about 0.4 to about 5, from about 0.4 to about 2, from about 0.4 to about 1, or from about 0.4 to about 0.8 mg/cm$^2$/day. Nonlimiting examples of the daily dosage include about 0.2, about 0.3, about 0.4, about 0.5, about 0.6, about 0.8, about 1.0, about 1.5, about 2.0, about 3.0, about 4.0 mg/cm$^2$/day, and any range between any two of the aforementioned values.

In some embodiments, the mean $C_{max,ss}$ is less than 2500, less than 2000, less than 1500, less than 1000, less than 500, less than 300, less than 200, less than 150, or less than 100 pg/mL. Nonlimiting examples of the mean $C_{max,ss}$ include about 80 pg/mL, about 100 pg/mL, about 120 pg/mL, about 150 pg/mL, about 200 pg/mL, about 250 pg/mL, about 300 pg/mL, about 500 pg/mL, about 1000 pg/mL, about 1500 pg/mL, about 2000 pg/mL, about 2500 pg/mL, about 3000 pg/mL, and any range between any two of the aforementioned values.

The formulation may be administered 1, 2, 3, 4 or 5 times a day. To achieve a desirable therapeutic effect with minimum skin irritation, various factors including the configuration of the formulation, the amounts of the active ingredient and excipients and the frequency of administration need to considered. In some embodiments, the daily dose ranges from about 0.5 to about 8 mg/cm$^2$/day, and the mean $C_{max,ss}$ is less than 150 pg/mL. In some embodiments, the formulation contains propylene glycol in an amount ranging from 5% to 7% by weight, carbomer in an amount ranging from 1.6% to 2.5% by weight, triethanolamine in an amount ranging from 0.6% to 1.0% by weight, and ethyl hydroxybenzoate in an amount ranging from 0.05% to 2% by weight. In some embodiments, the formulation contains propylene glycol in an amount of about 6% by weight carbomer in an amount of about 1.8% by weight, triethanolamine in an amount of about 0.8% by weight, and ethyl hydroxybenzoate in an amount of about 0.1% by weight.

In some embodiments, the formulation is administered twice a day. In some embodiments, the formulation is free from a permeation enhancer to reduce skin irritation.

The formulation may be various suitable forms such as a gel, an ointment, and a cream. In some embodiments, the formulation is a gel.

In some embodiments, the subject has been diagnosed with infantile hemangiomas. In some embodiments, the subject has been diagnosed with chronic venous leg ulcer.

Another aspect provides a method for treating infantile hemangiomas comprising topically administrating, to a patient in need thereof, a topical formulation comprising timolol maleate such that the timolol dose in topical administration is in the range of 0.4-15 mg/cm$^2$/day, timolol dosing frequency is in the range of 1-5 times/day, wherein after topical administration of timolol maleate on the disease lesion, at steady state the timolol plasma concentration in the patient is less than 3 ng/ml and $C_{max}/C_{min}$ ration is less than 2. The dosage, administration schedule and other PK paramgers can be the same as descried above.

In some embodiments, the timolol dose in topical administration to the patient in need thereof is in the range of 0.4-10 mg/cm$^2$/day; in some embodiments it is in the range of 0.5-8 mg/cm$^2$/day; in some embodiments it is in the range of 1.2-5 mg/cm$^2$/day;

In some embodiments, the timolol dosing frequency in topical administration to the patient in need thereof is in the range of 1-4 times/day; In some embodiments it is in the range of 2-3 times/day; in some embodiments it is 2 times/day.

In some embodiments, the duration of timolol treatment in topical administration to the patient in need thereof is in the range of 3-12 month.

The present invention also provides a pharmaceutical composition of timolol maleate, which comprises timolol maleate, pharmaceutical excipients and water, wherein pharmaceutical excipients contain carbomer accounting for 1.6~2.5% by weight, triethanolamine accounting for 0.6~1.0% by weight, propylene glycol accounting for 5~7% by weight and ethyl hydroxybenzoate accounting for 0.05~2% by weight, and the reminding is water. The pharmaceutical composition is preferably a gel.

EXAMPLES

Example 1

Various factors, including controlled release of the active ingredient, skin irritation and solubility of excipients, need to be considered to prepare a formulation suitable for topical administration. In this experiment, multiple formulations were prepared and examined.

The amount of the propylene glycol as a solvent is important.

It was observed that a low amount of (1%-4%) propylene glycol in the formulation, while contributing to decreased skin irritation, it also led to a reduced solubility of ethyl hydroxybenzoate in the formulation, and part of the ethyl hydroxybenzoate would precipitate in the form of floccules in a gel formulation when prepared by conventional addition method of ethyl hydroxybenzoate. As exemplified in the production process below, when ethyl hydroxybenzoate in propylene glycol solution was diluted with water first before adding to the bulk solution for mixing, the formulation exhibited improved profile. It was observed that a suitable amount of propylene glycol not only dissolved excipients such as ethyl hydroxybenzoate but also enhanced the antibacterial effect of ethyl hydroxybenzoate while offering some moisturizing function.

In the exemplified formulations below, the amount of propylene glycol was increased to 5%-7%. Furthermore, the carbomer level was 1.6~2.5%. The rate of drug release was slowed due to high gel viscosity, and meanwhile the $C_{max}$ of the active ingredient was reduced. The composition of new formulations is shown in table 1 and table 2.

TABLE 1

| | Formulated dosage (w/w) | | | |
| --- | --- | --- | --- | --- |
| Component | Formulation 1 | Formulation 2 | Formulation 3 | Formulation 4 |
| Timolol maleate | 1.36 | 1.36 | 1.36 | 1.36 |
| Ethyl hydroxybenzoate | 0.1 | 0.1 | 0.1 | 0.1 |
| Propylene glycol | 6 | 6 | 6 | 6 |
| Carbomer 980 | 2.5 | 2.5 | 2.5 | 2.5 |
| Triethanolamine | 1 | 1.5 | 2 | 2.5 |
| Purified water | 89.04 | 88.54 | 88.04 | 87.54 |
| Total | 100 | 100 | 100 | 100 |
| Viscosity (T-bar spindle D) | 19600 cp | 26800 cp | 27200 cp | 30000 cp |

TABLE 2

| | Formulated dosage (w/w) | | | |
| --- | --- | --- | --- | --- |
| Component | Formulation 5 | Formulation 6 | Formulation 7 | Formulation 8 |
| Timolol maleate | 0.68 | 0.68 | 0.68 | 0.68 |
| Ethyl hydroxybenzoate | 0.1 | 0.1 | 0.1 | 0.1 |
| Propylene glycol | 6 | 6 | 6 | 6 |
| Carbomer 980 | 1.8 | 1.8 | 1.8 | 1.8 |
| Triethanolamine | 0.6 | 0.8 | 1.3 | 1.8 |
| Purified water | 90.82 | 90.62 | 90.12 | 89.62 |
| Total | 100 | 100 | 100 | 100 |
| Viscosity (T-bar spindle C) | 27700 cp | 34600 cp | 39250 cp | 39950 cp |

The gel preparation process comprises the following steps:
1) Add a predetermined amount of timolol maleate in water, stir and dissolve to obtain a clear and transparent solution I;
2) Add a predetermined amount of carbomer to solution I and stir to make it fully swollen to obtain a well-dispersed solution II;

3) Add a predetermined amount of ethyl hydroxybenzoate to a formulated dosage or a predetermined amount of propylene glycol, stir and dissolve to obtain a clear and transparent solution III;
4) Add solution III to solution II, stir and mix well to obtain mixture V;
5) Add a predetermined amount of triethanolamine to the mixture V described in step 4), add the remaining amount of water and mix well to obtain the pharmaceutical composition of timolol maleate.

Example 2

This experiment examined the irritability of the prepared formulations to skin. The irritation of guinea pig skin by gels prepared with different formulations (Table 3) is compared with formulation 6 as below.

TABLE 3

| | Formulated dosage (w/w) | |
|---|---|---|
| Component | Formulation 9 | Formulation 10 |
| Timolol maleate | 0.68 | 0.68 |
| Ethyl hydroxybenzoate | 0.10 | 0.10 |
| Propylene glycol | 15.00 | 15.00 |
| Carbomer 980 | 0.75 | 0.75 |
| Triethanolamine | 0.75 | 0.75 |
| Azone | 1.00 | / |
| Purified water | 81.72 | 82.72 |
| Total | 100.00 | 100.00 |

Note:
Formulation 9 is a gel containing a transdermal penetration enhancer; Formulation 10 is a gel containing no transdermal penetration enhancer. Both formulations have high level of propylene glycol (15%).

The gels prepared by formulation 6, 9 and 10 were subjected to skin irritation tests on 12 guinea pigs, respectively. As can be seen in Table 4, 2 of the 12 guinea pigs in formulation 9 group showed skin irritation, 1 in formulation 10 group showed skin irritation, and no skin irritation reaction was observed in formulation 6 group. This experiment showed that 6% propylene glycol in the gel formulation led to a good safety profile.

TABLE 4

Incidence and severity of skin irritation after transdermal application of the drug

| Formulation | Formulation 9 | | Formulation 10 | | Formulation 6 | |
|---|---|---|---|---|---|---|
| | Administered site | Unadministered site | Administered site | Unadministered site | Administered site | Unadministered site |
| Number of animals | 12 | | 12 | | 12 | |
| Erythema and/crusting (score) | | | | | | |
| Slight erythema (1) | 3 | 0 | 2 | 0 | 0 | 0 |
| Visible erythema (2) | 1 | 0 | 1 | 0 | 0 | 0 |
| Moderate to severe erythema (3) | 1 | 0 | 0 | 0 | 0 | 0 |
| Severe erythema to crusting (4) | 0 | 0 | 0 | 0 | 0 | 0 |
| Crusting (5) | 0 | 0 | 0 | 0 | 0 | 0 |
| Edema (scoring) | | | | | | |
| Very slight edema (1) | 0 | 0 | 0 | 0 | 0 | 0 |
| Mild edema (raised areas with clear margins) (2) | 0 | 0 | 0 | 0 | 0 | 0 |
| Moderate edema (bulging by about 1.0 mm) (3) | 0 | 0 | 0 | 0 | 0 | 0 |
| Severe edema (bulging by more than 1.0 mm with extension beyond the exposed area) (4) | 0 | 0 | 0 | 0 | 0 | 0 |
| Number of animals showing skin toxicity (total | 2 (12) | 0 (12) | 1 (12) | 0 (12) | 0 (12) | 0 (12) |

TABLE 4-continued

Incidence and severity of skin irritation after transdermal application of the drug

| Formulation | Formulation 9 | Formulation 10 | Formulation 6 |
|---|---|---|---|
| number of animals) | | | |

NOTE:
The gel of a formulation is considered potentially dermatotoxic if at least one animal has a total skin score ≥2 on the administered site and a total skin score of <2 (no skin irritation) on the unadministered site.

Long-term toxicity experiments were carried out on minipigs for 26 weeks with the gels prepared by formulations 6, 9, and 10 each administered topically to the skin at 10 mg/kg bid, and applied for 6 hours in the morning and evening, respectively; and the drug concentrations in the blood of the minipigs were detected after 26 weeks to be 4.35-11.4 ng/ml, 72.4-193.5 ng/ml and 22.1-65.7 ng/ml, respectively, with no allergic reactions observed on the skin of the minipigs. It indicates that the transdermal penetration enhancer and a high content of propylene glycol can increase the timolol plasma concentration in infantile patients in the clinical use, increasing their risk of having systemic adverse reactions.

Example 3

Plasma concentrations of the active ingredient at different daily doses were investigated. Healthy subjects were applied with timolol (TM) gel on the back (area: 200 cm² (20×10 cm)) at an amount of about 8 g (timolol content: 40 mg (0.5% TM gel)) in the morning on Day 1 (about 8:00 a.m.), followed by a 2-day washout phase, then once a day (Group 1), twice a day (Group 2), or three times a day (Group 3), respectively, for 9 consecutive days. The results showed good safety and tolerability. All drug-related AEs in this study were mild, and most of the AEs were subjects' skin reactions after medication and chief complaint.

The average plasma concentration-time curve (linear) for single and multiple doses of TM gel are shown in FIG. 1. The average steady-state concentrations ($C_{avg,ss}$) of the three groups were 59.9±49.7 pg/mL, 106.8±62.6 pg/mL and 106.8±86.8 pg/mL, respectively. The steady-state maximum observed concentrations ($C_{max,ss}$) were 68.5±56.3 pg/mL, 121.3±69.9 pg/mL and 121.2±98.9 pg/mL, respectively. The steady-state trough concentrations ($C_{min,ss}$) were 48.0±41.0 pg/mL, 91.1±56.2 pg/mL and 93.8±75.3 pg/mL, respectively. The steady-state plasma concentrations were compared. It is surprised to find that steady-state plasma concentrations in Groups 2 and 3 were higher than that in Group 1, and there was no difference between Groups 2 and 3. These indicate that after the TM gel was locally administered for more than two times (0.4 mg/cm²/day), the absorption of the drug to the skin was saturated. Since Infantile hemangiomas is local disease, the treatment depends on the skin drug concentration, the dose by once daily (0.2 mg/cm²/day) may not be enough and dose by twice a day (0.4 mg/cm²/day) and three times a day (0.6 mg/cm²/day) may have the same efficacy due to the same saturated drug concentration in the skin.

Example 4

The clinical effectiveness of formulated timolol gel was investigated. A total of 168 infant patients aged 35-150 days with superficial hemangiomas were enrolled into the trieal. After obtaining the consent of their family members, the patients were randomized into 3 groups, 56 in each group. The infantile patients were subjected to a 6-month clinical trial of timolol gel (formulation 7) twice per day, three times per day and placebo gel, respectively, to evaluate the efficacy of the treatment by the success rate for IH treatment after 24 weeks of treatment, visual analog scoring, and the clinical changes in the color of the tumors of the patients during the treatment was also recorded as secondary endpoints.

Figure 2:
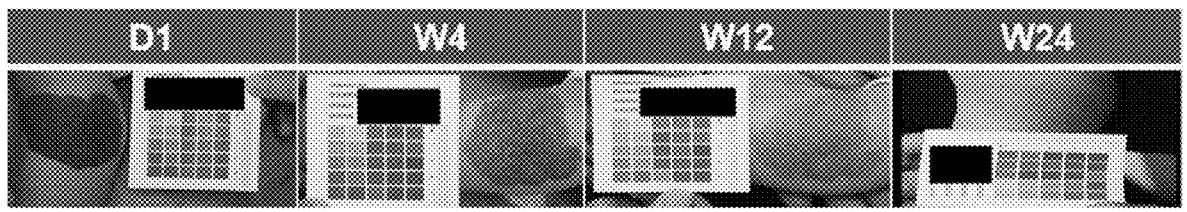
FIG. 2 shows the hemangiomas after success treatment in clinical trial with an example timolol gel formulation.

In the 24-week IH treatment, a total of 21 subjects in the 3 doses/day test group achieved complete/almost complete regression, with a success rate of 42.0% (21/50), and the 95% CI of 28.19%~56.79%; 29 subjects in the 2 doses/day test group achieved complete/almost complete regression, with a success rate of 55.8% (29/52), and the 95% CI of 41.33%~69.53%; 8 subjects in the placebo group achieved complete/almost complete regression, with a success rate of 15.1% (8/53), and the 95% CI of 6.75%~27.59%. The example photos of success treatment are shown in FIG. 2. Other secondary endpoints were consistent with those of the primary efficacy analysis.

All the dose in the clinical study is higher than 0.4 mg/cm²/d, with the range from 0.5-15 mg mg/cm²/d. Subjects were stratified by the daily dose/cm² in each group (on active ingredient basis: ≥0.5, <2.0 mg/cm²/d, ≥2.0, <4.0 mg/cm²/d and ≥4.0 mg/cm²/d), and the IH treatment success rates of the 24-week treatment were summarized in table 3. The results showed that no significant effect of daily dose/cm² in each group was observed on IH treatment success rate of the 24-week treatment. This agrees with the result form phase 1 study in Healthy subjects, which indicate that when dose is more than 0.4 mg/cm²/d, the skin is satured and the efficacy is similar.

TABLE 3

Summary of IH treatment success rates of the 24-week treatment stratified by different daily dose/cm2

| | 3 doses/day test group | | 2 doses/day test group | |
|---|---|---|---|---|
| Daily dose/cm² (mg/cm²/d) | n | Number of successful subjects (IH treatment success rate) | n | Number of successful subjects (IH treatment success rate) |
| ≥0.5, <2.0 | 11 | 5 (45.5%) | 20 | 10 (50.0%) |
| ≥2.0, <4.0 | 14 | 6 (42.9%) | 14 | 11 (78.6%) |
| ≥4.0 | 25 | 10 (40.0%) | 18 | 8 (44.4%) |
| Total | 50 | 21 (42.0%) | 52 | 29 (55.8%) |

Note:
The daily dose/cm² is calculated on active ingredient basis.

The IH treatment success rate was 15.1% (8/53) in the placebo group after the 24-week treatment in the centralized independent assessment).

The results of the safety analysis showed that timolol gel had the good systemic and local safety when being applied for treating superficial IH in the proliferative phase. The results of the PK analysis showed that the systemic exposure to timolol was at a low level after application of Timolol gel (formulation 7), and at steady state the timolol plasma concentration of all patients is less than 3 ng/ml with the median concentration of ~100 μg/ml and, which is much lower than the exposure of commercial Timolol eye drop in the pediatric population (3.5-35 ng/ml).

The embodiments above only express some implementation modes of the present invention, which are described in a more specific and detailed manner. However, they cannot be construed as limitations on the scope of the patent of the present invention. It should be noted that, for those skilled in the art, deformations and modifications can be made without departing from the ideas of the present invention, which are all within the scope of protection of the patent for the present invention. Therefore, the scope of protection of the patent for the present invention is subject to the appended claims.

The invention claimed is:

1. A method of providing a steady state mean timolol blood $C_{max,ss}$ less than 150 pg/mL in a human subject in need thereof, comprising administering topically to the subject a formulation comprising timolol maleate at a daily dose of timolol ranging from about 0.5 to about 8 mg/cm²/day, wherein the formulation is configured and the amount of the timolol maleate in the formulation is selected so that at steady state a ratio of $C_{max,SS}/C_{min,SS}$ is less than 2, wherein the formulation comprises timolol maleate, propylene glycol in an amount of about 6% by weight, carbomer in an amount of about 1.8% by weight, triethanolamine in an amount of about 0.8% by weight, and ethyl hydroxybenzoate in an amount of about 0.1% by weight, and water.

2. The method of claim 1, wherein the timolol maleate is in an amount ranging from about 0.5% to about 2.0% by weight in the formulation.

3. The method of claim 1, wherein the formulation is administered 1-5 times a day.

4. The method of claim 1, wherein the formulation is administered 2-3 times a day.

5. The method of claim 1, wherein the formulation is administered 2 times a day.

6. The method of claim 1, wherein the subject is of an age of 3-12 month.

7. The method of claim 1, wherein the subject has been diagnosed of infantile hemangiomas.

8. The method of claim 1, wherein the formulation is in the form of a gel.

9. The method of claim 1, wherein the formulation is free from a permeation enhancer.

10. The method of claim 1, wherein the subject has been diagnosed with chronic venous leg ulcer.

* * * * *